US00PP19538P2

(12) United States Plant Patent
Schwartz

(10) Patent No.: US PP19,538 P2
(45) Date of Patent: Dec. 2, 2008

(54) ***ASTER* PLANT NAMED 'VIBRANT DOME'**

(50) Latin Name: *Aster novae-angliae*
Varietal Denomination: Vibrant Dome

(76) Inventor: Bobbie Schwartz, 18405 Van Aken Blvd., Shaker Heights, OH (US) 44122

( * ) Notice: Subject to any disclaimer, the term of this patent is extended or adjusted under 35 U.S.C. 154(b) by 0 days.

(21) Appl. No.: 12/012,477

(22) Filed: Jan. 31, 2008

(51) Int. Cl.
*A01H 5/00* (2006.01)

(52) U.S. Cl. ..... Plt./355
(58) Field of Classification Search ..... Plt./355
See application file for complete search history.

*Primary Examiner*—Kent L. Bell
*Assistant Examiner*—Georgia Helmer
(74) *Attorney, Agent, or Firm*—C. A. Whealy

(57) ABSTRACT

A new and distinct cultivar of *Aster* plant named 'Vibrant Dome', characterized by its uniform, upright and mounded plant habit; freely branching growth habit; dark green-colored foliage; uniform and freely flowering habit; semi-double-type inflorescences with purple-colored ray florets; and food garden performance.

1 Drawing Sheet

Botanical designation: *Aster novae-angliae.*
Cultivar denomination: 'Vibrant Dome'.

BACKGROUND OF THE INVENTION

The present invention relates to a new and distinct cultivar of *Aster* plant, botanically known as *Aster novae-angliae* and hereinafter referred to by the name 'Vibrant Dome'.

The new *Aster* is a naturally-occurring whole plant mutation of the *Aster novae-angliae* cultivar Purple Dome, not patented. The new *Aster* was discovered and selected by the Inventor as a single flowering plant within a population of plants of the cultivar Purple Dome in a controlled greenhouse environment in Shaker Heights, Oh. during the fall of 2004. The selection of this plant was based on its unique ray floret color.

Asexual reproduction of the new *Aster* by vegetative tip cuttings was first conducted in Lancaster, Pa. in November, 2005. Asexual reproduction by cuttings has shown that the unique features of this new *Aster* are stable and reproduced true to type in successive generations.

SUMMARY OF THE INVENTION

Plants of the cultivar Vibrant Dome have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Vibrant Dome'. These characteristics in combination distinguish 'Vibrant Dome' as a new and distinct potted *Aster* cultivar:

1. Uniform, upright and mounded plant habit.
2. Freely branching growth habit.
3. Dark green-colored foliage.
4. Uniform and freely flowering habit.
5. Semi-double type inflorescences with purple-colored ray florets.
6. Good garden performance.

Plants of the new *Aster* differ from plants of the parent, the cultivar Purple Dome, primarily in ray floret color as plants of the cultivar Purple dome have darker purple-colored ray florets.

Plants of the new *Aster* can be compared to plants of the *Aster* cultivar Patricia Ballard, not patented. In side-by-side comparisons conducted in Lancaster, Pa., plants of the new *Aster* differed from plants of thhe cultivar Patricia Ballard in the following characteristics:

1. Plants of the new *Aster* were more compact and mounding than plants of the cultivar Patricia Ballard.
2. Plants of the new *Aster* were stronger than plants of the cultivar Patricia Ballard.
3. Plants of the new *Aster* and the cultivar Patricia Ballard differed in ray floret coloration.

BRIEF DESCRIPTION OF THE PHOTOGRAPHS

The accompanying photographs illustrate the overall appearance of the new *Aster*. These photographs show the colors as true as it is reasonably possible to obtain in colored reproductions of this type. Colors in the photographs may differ slightly from the color values cited in the detailed botanical description which accurately describe the colors of the new *Aster.*

The photograph at the bottom of the sheet comprises a side perspective view of a typical flowering plant of 'Vibrant Dome'.

The photograph at the top of the sheet is a close-up view of typical inflorescences of 'Vibrant Dome'.

DETAILED BOTANICAL DESCRIPTION

The aforementioned photographs and following observations and measurements describe plants grown during the summer and fall in Lancaster, Pa. in an outdoor nursery and under conditions and practices which approximate those generally used in commercial potted *Aster* production. During the production of the plants, day temperatures ranged from 18° C. to 35° C. and night temperatures ranged from 7° C. to 27° C. Rooted cuttings were planted in 20-cm containers, and exposed to natural season conditions. Plants used in the photographs and for the description were about ten months old. In the following description, color references are made to The Royal Horticultural Society Colour Chart, 1995 Edition, except where general terms of ordinary dictionary significance are used.

Botanical classification: *Aster novae-angliae* cultivar Vibrant Dome.

Parentage: Naturally occurring whole plant mutation of the *Aster novae-angliae* cultivar Purple Dome, not patented.

Propagation:

*Type.*—Terminal vegetative cuttings.

*Time to initiate roots, summer.*—About two days at temperatures of about 27° C.

*Time to initiate roots, winter.*—About four days at temperatures of about 21° C.

*Time to produce a rooted young plant, summer.*—About seven days at temperatures of about 27° C.

*Time to produce a rooted young plant, winter.*—About twelve days at temperatures of about 21° C.

*Root description.*—Medium thickness, fibrous; white in color.

*Rooting habit.*—Freely branching; dense.

Plant description:

*Appearance.*—Herbaceous semi-double-type potted *Aster*. Upright with lateral branches somewhat outwardly spreading; inverted triangle with uniformly mounded crown. Freely branching growth habit with about three primary lateral branches each with six to eight secondary branches; dense and full plants. Vigorous growth habit.

*Plant height.*—About 16 cm.

*Plant width.*—About 25 cm.

*Lateral branches.*—Length: About 12 cm. Diameter: About 6 mm. Internode length: About 9 mm. Strength: Strong. Texture: Densely pubescent, hirsute. Color: Close to 193A.

Foliage description:

*Arrangement.*—Alternate, simple; sessile.

*Length.*—About 8.2 cm.

*Width.*—About 2 cm.

*Shape.*—Oblong to lanceolate.

*Apex.*—Acute.

*Base.*—Auriculate; clasping.

*Margin.*—Entire.

*Texture, upper and lower surfaces.*—Pubescent; rough.

*Color.*—Developing foliage, upper and lower surfaces: Close to 137A. Fully expanded foliage, upper surface: Close to 147A; ventation, 147C. Fully expanded foliage, lower surface: Close to 137C; venation, 147B.

Inflorescence description:

*Appearance.*—Semi-double type inflorescence form with ligulate-shaped ray florets. Inflorescences borne in clusters of four to five per terminal above and beyond the foliage. Disk and ray florets arranged acropetally on a capitulum. Inflorescence not fragrant.

*Flowering response.*—Under natural conditions, plants flower in late summer/early fall in the Northern Hemisphere. Inflorescences persistent. Inflorescences last about four to five days on the plant.

*Quantity of inflorescences.*—Freely flowering, about eight to ten developing and open inflorescences per lateral stem.

*Inflorescence bud.*—Height: About 1 cm. Diameter: About 6 mm. Shape: Ovoid. Color: Close to 77A.

*Inflorescence size.*—Diameter: About 4 cm. Depth (height): About 2.4 cm. Diameter of disc: About 7 mm. Receptacle height: About 9 mm. Receptacle diameter: About 7 mm.

*Ray florets.*—Length: About 2.2 cm. Width: About 2 mm. Shape: Ligulate. Apex: Acute. Base: Attenuate. Margin: Entire.Texture, upper and lower surfaces: Smooth, glabrous, satiny. Orientation: Initially upright, then about 90° from vertical or perpendicular to peduncle; apices reflexing with development. Number of ray florets per inflorescence: About 52 arranged in about three whorls. Color: When opening, upper surface: Close to 72A. When opening, lower surface: Close to 72B. Fully opened, upper surface: Close to 77B. Fully opened, lower surface: Close to 77C.

*Disc florets.*—Arrangement: Massed at center of receptacle. Shape: Tubular, elongated. Apex: Five-pointed. Length: About 8 mm. Width: 1 mm. Number of disc florets per inforescence: About 64. Color, immature: Apex: Close to 72A. Mid-section: Close to 148D. Base: Close to 157A. Color, mature: Apex: Close to 77B. Mid-section: Close to 78D. Base: Close to 157A.

*Phyllaries.*—Number of phyllaries per inflorescence: About 44 arranged in about five whorls. Length: About 1 cm. Width: About 1 mm. Shape: Lanceolate. Apex: Acuminate. Base: Truncate. Texture, upper and lower surfaces: Pubescent. Color, upper and lower surfaces: Close to 147A.

*Peduncles.*—Length: First peduncle: About 1.8 cm. Fourth peduncle: About 1.3 cm. Diameter (first peduncle): About 1.5 mm. Angle: Upright to about 45° from vertical. Strength: Strong, flexible. Texture: Pubescent. Color: Close to 147C.

*Reproductive organs.*—Androecium: Present on disc florets only. Filament length: About 1 mm. Filament color: Close to 157D. Anther shape: Slender, elongated oblong. Anther length: About 2 mm. Anther color: Close to 177D. Pollen amount: None observed. Gynoecium: Present on both ray and disc florets. Pistil length: About 7 mm. Stigma shape: Bi-parted. Stigma color: Close to 151A. Style length: About 4 mm. Style color: Close to 150C. Ovary color: Close to 157D.

*Seed/fruit.*—Seed and fruit production has not been observed.

Disease/pest resistance: Resistance to pathogens and pests common to *Asters* has not been observed on plants grown under commercial conditions.

Garden performance: Plants of the new *Aster* have been observed to be rain and wind tolerant and to tolerate temperatures from 2° C. to about 35° C.

It is claimed:

1. A new and distinct *Aster* plant named 'Vibrant Dome' as illustrated and described.

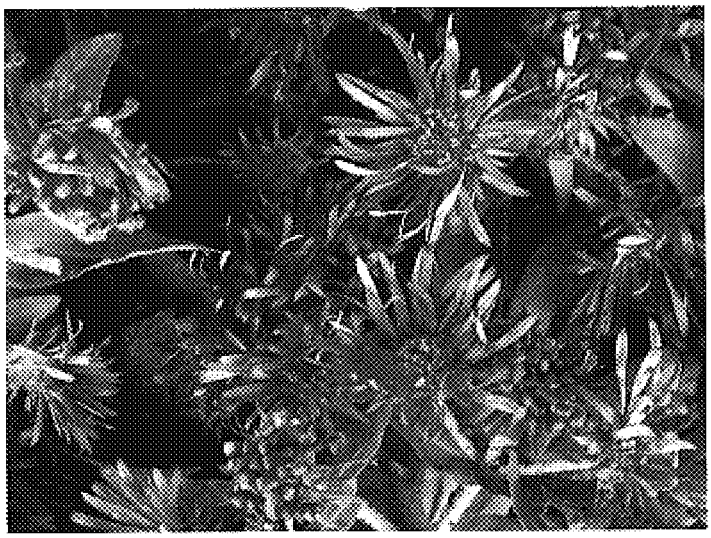
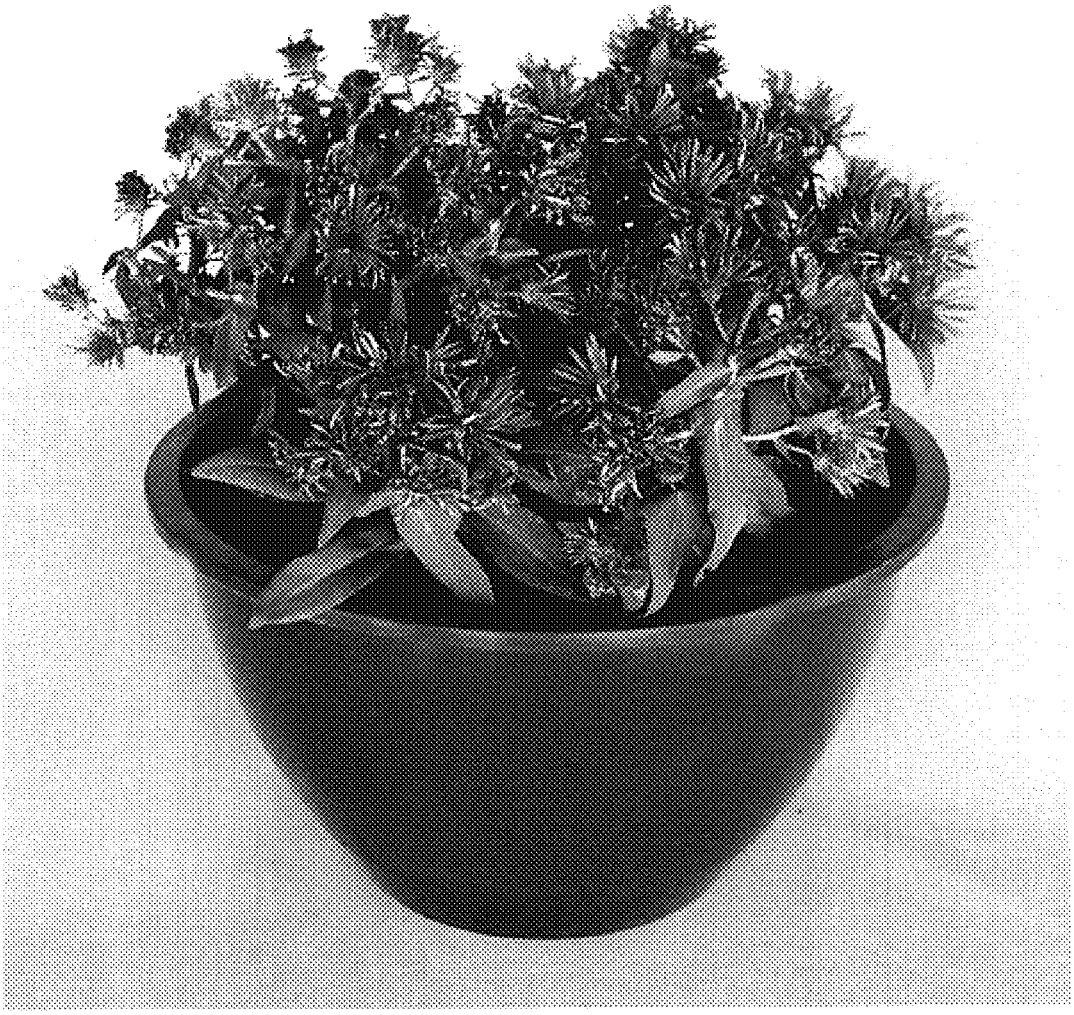

* * * * *